United States Patent [19]

Blüm

[11] Patent Number: 4,536,348
[45] Date of Patent: Aug. 20, 1985

[54] DIHYDROXYALKANE DIPHOSPHONIC ACIDS

[75] Inventor: Helmut Blüm, Duesseldorf, Fed. Rep. of Germany

[73] Assignee: Henkel Kommanditgesellschaft auf Aktien, Dusseldorf, Fed. Rep. of Germany

[21] Appl. No.: 649,868

[22] Filed: Sep. 12, 1984

[30] Foreign Application Priority Data

Sep. 22, 1983 [DE] Fed. Rep. of Germany ....... 3334211

[51] Int. Cl.³ .......................... C07F 9/38; A61K 31/66
[52] U.S. Cl. .............................. 260/502.4 P; 252/32.5
[58] Field of Search .................. 260/502.4 P, 502.4 A

[56] References Cited

U.S. PATENT DOCUMENTS

| 3,525,782 | 8/1970 | Jacques | 260/502.4 P |
|---|---|---|---|
| 3,551,480 | 12/1970 | Germscheid et al. | 200/502.4 A |
| 4,054,598 | 10/1977 | Blum et al. | 260/502.5 C |
| 4,064,164 | 12/1977 | Blum et al. | 260/502.5 C |
| 4,069,246 | 1/1978 | Blum et al. | 260/502.4 P |
| 4,267,108 | 5/1981 | Blum et al. | 260/502.5 C |
| 4,327,039 | 4/1982 | Blum et al. | 260/502.5 C |
| 4,407,761 | 10/1983 | Blum et al. | 260/502.5 C |

FOREIGN PATENT DOCUMENTS

| 82472 | 6/1983 | European Pat. Off. | 260/502.5 C |
|---|---|---|---|
| 3016289 | 10/1981 | Fed. Rep. of Germany | 260/502.5 C |

OTHER PUBLICATIONS

Nicholson et al., J. Org. Chem., vol. 36, No. 24, 1971, pp. 3843–3845.

Primary Examiner—J. E. Evans
Attorney, Agent, or Firm—Ernest G. Szoke; Henry E. Millson, Jr.; Mark A. Greenfield

[57] ABSTRACT

α,ω-dihydroxyalkane-α,α-diphosphonic acids of the formula $$R\text{—CH(OH)—(CH}_2)_n\text{—C(OH)}(PO_3H_2)_2 \qquad (I)$$

wherein R represents a phenyl radical, a substituted phenyl radical, or a hydrogen atom, and n is an integer of from 1 to 9, and water-soluble salts thereof, and to compositions containing them. The above diphosphonic acids are produced by reacting ω-amino-α-hydroxyalkane-α,α-diphosphonic acids with nitrous acid or a nitrous acid producing compound.

4 Claims, No Drawings

DIHYDROXYALKANE DIPHOSPHONIC ACIDS

BACKGROUND OF THE INVENTION

This invention relates to $\alpha,\omega$-dihydroxyalkane-$\alpha,\alpha$-diphosphonic acids, to water-soluble salts thereof, and to compositions containing them.

DESCRIPTION OF THE INVENTION

The $\alpha,\omega$-dihydroxyalkane-$\alpha,\alpha$-diphosphonic acids of the invention have the following general formula:

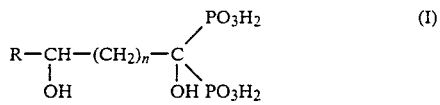

in which R represents a phenyl radical, a substituted phenyl radical, or an H-atom, and n is an integer of from 1 to 9, and water-soluble salts thereof. When R is a substituted phenyl radical, the substituents can be one or more of halogen, e.g. chlorine, bromine, iodine, or fluorine; $C_1$–$C_6$ alkyl, e.g. methyl, ethyl, propyl, isopropyl, etc.; or hydroxyl.

The new diphosphonic acids are produced by reacting $\omega$-amino-$\alpha$-hydroxyalkane-$\alpha,\alpha$-diphosphonic acids of the formula:

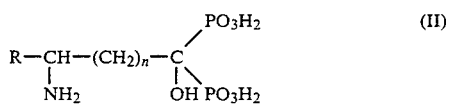

wherein R and n have the meanings given above for the compounds of Formula I, with nitrous acid. In general, the process of the invention is carried out by introducing the aminophosphonic acid of Formula II in aqueous solution or suspension into a reaction vessel, followed by the addition of nitrous acid slowly or in portions, i.e. over a period of several hours or more, for example, over a period of from about 10 to about 15 hours. The nitrous acid is preferably used in the form of an aqueous sodium nitrite solution; the nitrous acid being formed as an intermediate stage in the course of the reaction. It is generally not necessary to add another acid to the reaction mixture because the pH-range required for the formation of nitrous acid is usually maintained by the diphosphonic acid initially introduced to the reaction vessel.

Instead of sodium nitrite, other substances can be employed that form nitrous acid during the reaction, such as for example $N_2O_3$ or NOCl. Where gaseous reagents such as these are used, they are introduced into the aqueous solution or suspension of the compound of Formula II.

Temperatures above the room temperature are maintained in the reaction mixture during the reaction. Preferred temperatures are in the range of from about 40° C. to about 60° C., with temperatures of about 50° C. being particularly preferred.

To ensure that the aminoalkane diphosphonic acids used are fully reacted to form the desired end products, it is advantageous to use an excess of nitrous acid or sodium nitrite of from three to four times the molar quantity, based on the quantity of aminoalkane diphosphonic acid. A further increase in that excess can also be employed, and even a smaller excess leads to the required end products of Formula I. The slow addition of the reaction component "$HNO_2$" to the reaction mixture is also of advantage in increasing the yield of desired end product.

The end products of Formula I can be isolated by various methods:

If the free acid form of the compound of Formula I is required as the end product, the reaction product obtained is freed from cations by treatment with an acidic ion exchanger resin and then concentrated, resulting in formation of the expected diphosphonic acid.

On the other hand, the dihydroxy diphosphonic acids of the invention can also be isolated in the form of their water-soluble salts, i.e. in particular their alkali metal, ammonium, or alkanolamine, e.g. mono, di, or triethanolamine, propanolamine, etc. salts, preferably their sodium or potassium salts.

For example, where sodium nitrite is used, the sodium salt can be obtained by adjusting the pH-value of the reaction product to approximately 4.8, for example using dilute sodium hydroxide, followed by precipitation with a solvent, such as acetone or methanol.

If it is desired to obtain other salts of the dihydroxy diphosphonic acid, other cations present in the reaction mixture, such as sodium ions for example, are removed using an acidic ion exchanger resin before neutralization with the base having the desired cation.

If the reaction product still contains unreacted aminodiphosphonic acid, which may readily be established by chromatography, the clear reaction solution is treated with an acidic ion exchanger resin—before isolation of the end product—and then concentrated; the less soluble aminodiphosphonic acid precipitating from the solution, which can then be separated off.

The reaction of certain primary alkylamines with nitrous acid to form the corresponding compounds containing hydroxyl groups is a known reaction mechanism. In that instance, however, unwanted secondary products, such as for example those containing olefinic double bonds, are generally formed in considerable quantities.

It has surprisingly been found that, where the reaction is carried out according to the above-described process of the invention, no compounds containing olefinic double bonds and virtually no other secondary products are formed. The desired dihydroxyalkane diphosphonic acids are obtained almost exclusively as the reaction product.

The new dihydroxyalkane diphosphonic acids and their water-soluble salts show outstanding complexing power with respect to divalent and polyvalent metal ions, such as for example those of Ca, Mg, Cu, Fe, Cr and others, at various temperatures and pH-values. In particular, they show a particularly high calcium binding capacity which is better than that of the analogous compounds containing amino groups, as shown in the examples using the Hampshire Test.

Accordingly, the new dihydroxyalkane diphosphonic acids and their water-soluble salts are useful as complexing agents and sequestering agents.

The following compounds are examples of the new dihydroxyalkane diphosphonic acids of the invention:

1,3-dihydroxypropane-1,1-diphosphonic acid,
1,4-dihydroxybutane-1,1-diphosphonic acid,
1,5-dihydroxypentane-1,1-diphosphonic acid,
1,6-dihydroxyhexane-1,1-diphosphonic acid,
1,11-dihydroxyundecane-1,1-diphosphonic acid,
1,3-dihydroxy-3-phenylpropane-1,1-diphosphonic acid (in which the phenyl radical can be substituted, for example, by halogen, alkyl radicals, and/or hydroxyl groups), and their corresponding water-soluble salts.

Of these compounds, compounds corresponding to Formula I in which R=H and n=1-4 are preferred, and the compounds 1,3-dihydroxypropane-1,1-diphosphonic acid, and 1,6-dihydroxyhexane-1,1-diphosphonic acid, and their water-soluble salts are most preferred. The latter compounds show considerably greater sequestering power than other compounds of Formula I.

The new diphosphonic acids and their water-soluble salts are distinguished not only by their outstanding complexing power but alsol by their strong threshold activity, i.e. they are able to prevent the precipitation of sparingly soluble alkaline-earth metal salts, even in seeding quantities, i.e. substoichiometric quantities.

The new dihydroxyalkane diphosphonic acids and their water-soluble salts can be used as complexing agents for a wide variety of applications. For example, they can be used in combination with standard agents used in processes involved in softening water, in which case their above-mentioned threshold activity plays an important part. Accordingly, there is no need to use stoichiometric quantities; instead, precipitations of calcite can be retarded even with substoichiometric quantities.

They are also eminently suitable for use as corrosion and concretion inhibitors for cooling water, particularly in combination with known additives.

The new diphosphonic acids can also be used, for example, for removing incrustations from fabrics in which alkaline-earth metal salts have accumulated, and for reducing the accumulation of ash in fabrics. Finally, they can be used as builders with complexing properties in detergents and cleaners in quantities of from about 0.5 to about 10 wt. %, based on the weight of the detergent or cleaner, and can be employed in combination with known anion-active, cation-active or non-ionic wetting agents. In addition, they can be used in combination with caustic alkalis, alkali carbonates, silicates, phosphates or borates.

By virtue of their high complexing power, the acids of the invention and their salts can also be used with advantage in systems in which heavy-metal cations, for example copper ions, trigger undesirable effects including, for example, the decomposition of per compounds in bleaches and the discoloration and rancidity of fats and soaps.

They are also suitable for use in cleaning processes for hard objects, such as metal or glass. In this connection, they are particularly suitable for use as additives to bottle washing preparations.

The products according to the invention are also suitable for pharmaceutical purposes, particularly for treating disturbances in the calcium or phosphate metabolism in mammals and the illnesses associated therewith. Quantities of from about 1 to about 50 mg per kg body weight can be employed.

In addition, the new diphosphonic acids and their water-soluble salts can be used in cosmetic preparations, such as in toothpastes, mouthwashes and similar products, since they considerably reduce or inhibit the formation of tartar. Quantities of from about 0.5 to about 10 wt. % based on the weight of the cosmetic preparation are suitable for this use.

Finally, the new phosphonic acids are also suitable for the production of $99^m$-technetium radiodiagnostic preparations.

The invention is illustrated by but in no way limited to the following Examples.

EXAMPLE 1

0.1 mole of 3-amino-1-hydroxypropane-1,1-diphosphonic acid was suspended in 300 ml of water, followed by the dropwise addition over a period of 12 hours of 0.4 mole of 5% sodium nitrite solution. To remove small unreacted residues of starting compound, the clear reaction solution was treated with an acidic exchanger resin and then concentrated and the sparingly soluble aminodiphosphonic acid was separated off.

To isolate the end product in the form of the $Na_2$-salt, the filtrate was adjusted to pH 4.8 with dilute sodium hydroxide and the disodium-1,3-dihydroxypropane-1,1-diphosphonate precipitated with acetone. The salt was dried in vacuo at 50° C. Yield: 85%.

Elemental analysis: Calculated: P: 2.00: C: 3.14: Na: 2.08; Observed: (2: C: 3: Na: 2).

EXAMPLE 2

0.4 mole of sodium nitrite solution was added dropwise over a period of 15 hours to a suspension of 0.1 mole of 3-amino-3-phenyl-1-hydroxypropane-1,1-diphosphonic acid in 250 ml of water after heating to 50° c.

The reaction solution was then freed from $Na^+$-ions by treatment with acidic exchanger resin and concentrated. 62% of 3-phenyl-1,3-dihydroxypropane-1,1-diphosphonic acid was obtained from the concentrated solution. M.p. 132° C.

elemental analysis: Calculated: C: 34.6%; H: 5.01% P: 19.9%; Observed: C: (34.62); H: (4.49) P: (19.87).

EXAMPLE 3

0.1 mole of 6-amino-1-hydroxyhexane-1,1-diphosphonic acid was reacted using the same process and reactants as in Example 1 and then stirred for 10 hours to complete deamination. Further working up as in Example 1 resulted in separation of the $Na_2$-salt of 1,6-dihydroxyhexane-1,1-diphosphonic acid in a yield of more than 80%.

Elemental analysis: Calculated: P: 2.00: C: 6.18: Na: 2.01, Observed: P: (2: C: 6: Na: 2).

EXAMPLE 4

In the same manner as in Example 1, a suspension of 0.1 mole of 11-amino-1-hydroxyundecane-1,1-diphosphonic acid was treated with 0.4 mole of a sodium nitrite solution and stirred for several hours at 50° C. Any undissolved starting compound was then filtered off and the filtrate adjusted to pH 1 with conc. hydrochloric acid, resulting in the separation of an oil which, after drying in vacuo, was identified as 1,11-dihydroxyundecane-1,1-diphosphonic acid. Yield: 41%. M.p. 112° C.

Elemental analysis: Calculated: C: 38.4%; H: 7.44% P: 17.6%; Observed: C: (37.93) H: (7.47) P: (17.82).

EXAMPLE 5

Hampshire Test for determining calcium binding power at pH 11.

Approximately 1000 mg of the diphosphonic acids given below were dissolved in 80–90 ml of water and adjusted to pH 11 with sodium hydroxide, followed by the addition of 10 ml of a 2% soda solution. A calcium salt solution (36.8 g of CaCl$_2$.2H$_2$O/L) was then slowly added dropwise until permanent clouding was obtained.

The results are set out in the following Table:

| Substance | mg of CaCO$_3$ per g of acid |
|---|---|
| 1,3-dihydroxypropane-1,1-diphosphonic acid | 632 |
| Comparison: | |
| 3-amino-1-hydroxypropane-1,1-diphosphonic acid | 472 |
| 1,6-dihydroxyhexane-1,1-diphosphonic acid | 940 |
| Comparison: | |
| 6-amino-1-hydroxyhexane-1,1-diphosphonic acid | 420 |

The results show that a considerably larger quantity of CaCO$_3$ is completely held in solution by complexing with the diphosphonic acids of the invention than with the same quantity of the comparison substance.

EXAMPLE 6

The threshold activity of the dihydroxyalkane diphosphonic acids is shown in the following Table. The values show that calcium sulfate is still inhibited up to a seeding quantity of 1 ppm.

To determine threshold activity, 50 ml of a calcium salt solution (11.1 g of CaCl$_2$.2H2O/L and 7.5 g of NaCl/L) and 50 ml of a sulfate solution (10.66 g of Na$_2$SO$_4$/L and 7.5 g of NaCl/L) were added to the seeding quantities indicated in the table and the mixtures left standing for 72 hours at 70° C.

The proportion of calcium ions remaining in solution was then determined.

| Dihydroxyalkane diphosphonic acid | Gypsum inhibition in mg/L | | | | |
|---|---|---|---|---|---|
| | 1 ppm | 3 ppm | 5 ppm | 10 ppm | 20 ppm |
| 1 | 4814 | 5005 | 4910 | 4978 | 4964 |
| 2 | 4624 | 5114 | 5222 | 5236 | 5209 |
| 3 | 3713 | 3822 | 3917 | 4570 | 5127 |

Blank test without inhibitor: Observed: 3522, calculated: 5134

1 = 1,3-dihydroxypropane-1,1-diphosphonic acid
2 = 1,6-dihydroxyhexane-1,1-diphosphonic acid
3 = 1,3-dihydroxy-3-phenylpropane-1,1-diphosphonic acid

EXAMPLE 7

When the dihydroxyalkane diphosphonic acids or their pharmaceutically acceptable salts are used in oral and dental hygiene preparations, the formation of tartar is considerably reduced or inhibited. The pH-values of the mouthwashes or toothpastes can vary from pH 5 to 9.

The following formulations, for example, are suitable formulations for toothpastes:

| a. | |
|---|---|
| Glycerine | 60.0 parts by weight |
| Water | 13.5 |
| Sodium carboxymethyl cellulose | 0.6 |
| Silica xerogel | 20.0 |
| Sodium lauryl sulfate | 2.0 |
| Ethereal oils | 1.0 |
| Sweetener | 0.4 |
| 1,3-dihydroxypropane-1,1-diphosphonic acid | 2.5 |
| b. | |
| Glycerine | 30.0 parts by weight |
| Water | 18.5 |
| Sodium carboxymethyl cellulose | 1.0 |
| Aluminium hydroxide | 44.0 |
| Sodium lauryl sulfate | 1.0 |
| Silica, pyrogenic | 1.5 |
| Ethereal oils | 1.5 |
| Sweetener | 0.5 |
| 1,6-dihydroxyhexane-1,1-diphosphonic acid | 2.0 |

The following composition, for example, is a suitable formulation for a mouthwash:

| | |
|---|---|
| Ethyl alcohol | 19.5 parts by weight |
| Glycerine | 7.5 |
| Water | 70.0 |
| Ethereal oils | 0.2 |
| Sodium lauryl sulfate | 0.1 |
| Antiseptic (chlorthymol) | 0.1 |
| Sweetener | 0.1 |
| 1,3-dihydroxypropane-1,1-diphosphonic acid | 2.5 |

By regular use of the toothpastes and/or mouthwashes containing sodium salts of the diphosphonic acids of the invention, the formation of tartar can be significantly reduced and the development of hard, compact tooth coatings largely prevented.

What is claimed is:

1. An α,ω-dihydroxyalkane-α,α-diphosphonic acid of the formula:

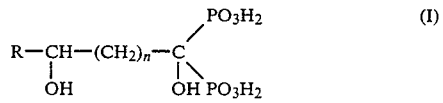

in which R represents hydrogen, phenyl, or a substituted phenyl wherein the substituents on the substituted phenyl are at least one of halogen, C$_1$-C$_6$ alkyl, and hydroxyl, and n is an integer of from 1 to 9, or a water-soluble salt thereof.

2. A compound in accordance with claim 1 wherein R is hydrogen, and n is an integer of from 1 to 4.

3. A compound in accordance with claim 1 which is 1,3-dihydroxypropane-1,1-diphosphonic acid or a water-soluble salt thereof.

4. A compound in accordance with claim 1 which is 1,6-dihydroxyhexane-1,1-diphosphonic acid or a water-soluble salt thereof.

* * * * *